US005698766A

United States Patent [19]
Julius et al.

[11] Patent Number: 5,698,766
[45] Date of Patent: Dec. 16, 1997

[54] TRANSGENIC ANIMAL MODEL FOR TESTING DRUGS FOR TREATING EATING DISORDERS AND EPILEPSY

[75] Inventors: David J. Julius; Laurence H. Tecott; Linda M. Sun, all of San Francisco, Calif.

[73] Assignee: The Regents of the University of California, Oakland, Calif.

[21] Appl. No.: 417,592

[22] Filed: Apr. 5, 1995

[51] Int. Cl.$^6$ .............................. C07H 21/04; C12N 5/06; C12N 15/06; C12Q 1/68
[52] U.S. Cl. .............................. 800/2; 435/6; 435/172.3; 435/240.21; 435/34; 435/70; 800/2; 800/DIG. 2; 800/DIG. 4; 536/23.5
[58] Field of Search .............................. 800/2; 530/350; 435/172.3; 514/44; 424/9.1

[56] References Cited

U.S. PATENT DOCUMENTS

| | | | |
|---|---|---|---|
| 4,873,191 | 10/1989 | Wagner et al. | 435/172.3 |
| 4,985,352 | 1/1991 | Julius et al. | 435/6 |
| 5,387,742 | 2/1995 | Cordell | 800/2 |

FOREIGN PATENT DOCUMENTS

| | | | |
|---|---|---|---|
| 2 699 922 | 12/1992 | France | C07K 13/00 |
| WO 91/17174 | 11/1991 | WIPO | C07H 21/00 |
| WO 93/11147 | 6/1993 | WIPO | C07H 21/00 |
| WO 93/14201 | 7/1993 | WIPO | C12N 15/00 |
| WO 94/14957 | 7/1994 | WIPO | C12N 15/00 |
| WO 94/16067 | 7/1994 | WIPO | C12N 15/12 |
| WO 94/21670 | 9/1994 | WIPO | C07K 5/00 |

OTHER PUBLICATIONS

Fields, H. (1984). Advances in Pain Research and Therapy 6, 241–252.
Milatovich et al (1992). Human Mol. Gen. 1, 681–684.
Hartig, P. et al (1990). "The 5–HT$_{1C}$ Receptor" in Annals of the N.Y. Academy of Sciences, vol. 600, pp. 149–167.
Heath, J. et al (1995). Current Biology 5(9), 997–999.
Curzon, G. (1990). "Serotonin and Appetite" in Annals of the N.Y. Academy of Sciences, vol. 600, 521–531.
Leibowitz, S. (1995). Obesity Research 3, Suppl. 4, 5735–5895. (Abstract only).
Bradley, A. et al (1992). BioTechnology, 10, 534–539.
Lucas, J. et al (1995). Trends in Pharmacological Sciences 16, 246–252.
Kao, H–T et al (1992). FEBS Letters, 307 (3), 324–328.
Sandou, F. et al (1994) Science 265, 1875–1877.
Yu, L et al (1991). Molecular Brain Research 11, 143–9.
Sambrook, J. et al (1989). Molecular Cloning, A Laboratory Manual, 2nd ed. pp. 15.51–15.52.
Orloff et al., "Timed Intravenous Infusion of Metrazol and Strychnine for Testing Anticonvulsant Drugs" *Proc. Soc. Exper. Biol. Med.* 70:254–257 (Jan.–Apr. 1949).
Jobe et al., "Role of Brain 5–Hydroxytryptamine in Audiogenic Seizure in the Rat" *Life Sciences* 13:1–13 (1973).
Kilian and Frey, "Central Monoamines and Convulsive Thresholds in Mice and Rats" *Neuropharmacology* 12:681–692(1973).

Samanin et al., "m–Chlorophenylpiperazine: A Central Serotonin Agonist Causing Powerful Anorexia in Rats," *Schm. Arch. Pharmacol.* 308:159–163 (1979).
White and Neuman, "Facilitation of Spinal Motoneurone Excitability by 5–HY–Droxytryptamine and Noradrenaline" *Brain Research* 188:119–127 (1980).
Kravitz et al., "Amines and a Peptide as Neurohormones in Lobsters: Actions on Neuromuscular Preparations and Preliminary Behavioural Studies" *J. Exp. Biol.* 89:159–175 (1980).
Aghajanian, G. K., "The Modulatory Role of serotonin at Multiple Receptors in Brain" (*MIT Press*, Cambridge Mass., 1981) pp. 156–185.
Siegelbaum et al., "Serotonin and Cyclic AMP Close Single K$^+$ Channels in Aplysia Sensory Neurones" *Nature* 299:413–417 (Sep. 1982).
Gundersen et al., "Serotonin Receptors Induced by Exogenous Messenger RNA in Xenopus Oocytes" *Proc. R. Soc. Lond.* 219:103–109 (1983).
Jacobs, B.L., "Postsynaptic Serotonergic Action of Hallucinogens," *Hallucinogens: Neurochemical, Behavioral, and Clinical Perspectives*, pp. 183–202 (1984).
de Courcelles et al. "Evidence That Phospholipid Turnover Is the Signal Transducing System Coupled to Serotonin–S$_2$ Receptor Sites" *J. Biol. Chem.* 260:7603–7608 (Jun. 1985).
Takaki, J. et al., "Specific Antagonism of Enteric Neural Serotonin Receptors by Dipeptides of 5–Hydroxytryptophan: Evidence that Serotonin Is a Mediator of Slot Synaptic Excitation in the Myenteric Plexus" *J. Neuroscience* 5:1769–1780 (Jul. 1985).
Sparks and Buckholtz, "Combined Inhibition of Serotonin Uptake and Oxidative Deamination Attenuates Audiogenic Seizures in DBA/2J Mice" *Pharmacology Biochem. & Behav.* 23:753–757 (Nov. 1985).
Weiss et al., "Serotonin 5–HT, Receptors Mediate Inhibition of Cycle AMP Production in Neurons" *European J. of Pharm.* 120:227–230 (Jan. 1986).
Conn et al., "A Unique Serotonin Receptor in Choroid Plexus is Linked to Phosphatidylinositol Turnover" *Proc. Natl. Acad. Sci.* 83:4086–4088 (May 1986).

(List continued on next page.)

*Primary Examiner*—Brian R. Stanton
*Assistant Examiner*—Nancy Axelrod
*Attorney, Agent, or Firm*—Karl Bozicevic; Pamela J. Sherwood; Fish & Richardson P.C.

[57] ABSTRACT

A transgenic, non-human animal model is disclosed which lacks receptors which mediate some of the central nervous system (CNS) actions of serotonin. The animal is preferably from a genus selected from the group consisting of Mus (e.g., mice), Rattus (e.g., rats), Oryctologus (e.g., rabbits) and Mesocricetus (e.g., hamsters). More preferably the animal is a mouse which lacks 5HT$_{2c}$ receptors. Animals lacking such receptors are overweight due to abnormal control of feeding behavior and are prone to spontaneous death from seizures. Thus, such animals provide an animal model for the testing of drugs which are potentially useful in the treatment of eating disorders and diseases such as epilepsy which result in seizures.

6 Claims, 7 Drawing Sheets

OTHER PUBLICATIONS

Andrade et al., "A G Protein Couples Serotonin and GABA$_B$ Receptors to the Same Channels in Hippocampus" *Science* 234:1161–1300 (Dec. 1986).

De Vivo and Maayani, "Characterization of the 5–Hydroxytryptamine$_{1A}$ Receptor–Mediated Inhibition of Forskolin–Stimulated Adenylate Cyclase Activity in Guinea Pig and Rat Hippocampal Membranes[1]" *J. Pharmacol. and Exper. Ther.* 238:248–253 (1986).

Lubbert et al., "Rat Brain 5–HT$_{1C}$ Receptors Are Encoded by a 5–6 kbase mRNA Size Class and Are Functionally Expressed in Injected Xenopus Oocytes" *J. Neuroscience* 7(4):1159–1165 (Apr. 1987).

Takahashi et al., "Rat Brain Serotonin Receptors in Xenopus Oocytes are Coupled by Intracellular Calcium to Endogenous Channels" *Proc. Natl. Acad. Sci.* 84:5063–5067 (Jul. 1987).

Andrade and Nicoll, "Pharmacologically Distinct Actions of Serotonin on Single Pyramidal Neurones of the Rat Hippocampus Recorded In Vitro" *J. Physiol.* 394:99–124 (1987).

Hoyer and Schoeffter, "5–HT$_{1D}$ Receptor–mediated Inhibition of Forskolin–stimulated Adenylate Cyclase Activity in Calf Substantia Nigra" *European J. of Pharmacol.* 147:145–147 (Feb. 1988).

Thomas et al., "The Expression of Transthyretin mRNA in the Developing Rat Brain" *Develop. Biol.* 128:415–427 (1988).

Peroutka, Stephen J., "5–Hydroxytryptamine Receptor Subtypes" *Ann. Rev. Neurosci.* 11:45–60 (1988).

Mansour et al., "Disruption of the Proto–oncogene int–2 in Mouse Embryo–derived Stem Cells: A General Strategy for Targeting Mutations to Non–selectable Genes" *Nature* 336:348–352 (Nov. 1988).

Parkinson and Weingarten "Dissociative Analysis of Ventromedial Hypothalamic Obesity Syndrome" *Am. Phys. Soc.* 259:R829–R835 (Oct. 1990).

Kennett & Curzon, "Potencies of Antagonists Indicate that 5–HT$_{1C}$ Receptors Mediate 1–3(chlorophenyl)piperazine–induced Hypophagis" *Br. J. Pharmacol.* 103:2016–2020 (Aug. 1991).

Sleight et al., "Serotonin Receptor Subtypes: Basic and Clinical Aspects" (eds. Peroutka, S.J.) 211–227 (Wiley–Liss, New York, NY (1991).

Himms–Hagen, "Neural Control of Brown Adipose Tissue Thermogenesis, Hypertrophy, and Atrophy," *Frontiers in Neuroendocrinology* 12:38–93 (1991).

Blunell, "Serotonin and the biology of feeding," *Am. J. Clin. Nutr.* 55:155S–159S (1992).

Tecott et al., "Nervous System Distribution of the Serotonin 5–HT$_3$ Receptor mRNA" *Proc. Natl. Acad. Sci.* 90:1430–1434 (Feb. 1993).

Kitchener and Dourish, "An Examination of the Behavioural Specificity of Hypophagia Induced by 5–HT$_{1B}$, 5–HT$_{1C}$ and 5–HT$_2$ Receptor Agonists Using the Post–prandial Satiety Sequence in Rats" *Psychopharm.* 113:369–377 (Jan. 1994).

Friedman and Leibel, "Tackling a Weighty Problem" *Cell* 69:217–220 (Apr. 1992).

Tecott and Julius, "A New Wave of Serotonin Receptors" *Current Opin. Neurobiol.* 3:310–315 (Jun. 1993).

Wurtman et al., "Dexfenfluramine, Fluoxetine, and Weight Loss Among Female Carbohydrate Cravers" *Neuropsychopharm.* 9:201–210 (1993).

Pompeiano et al., "Distribution of the Serotonin 5–HT$_2$ Receptor Family mRNAs: Comparison between 5–HT$_{2A}$ and 5–HT$_{2C}$ Receptors" *Mol. Brain Res.* 23:163–178 (1994).

Flier, Jeffrey, "The Adipocyte: Storage Depot or Node on the Energy Information Superhighway" *Cell* 80:15–18 (Jan. 1995).

Brake et al., "New Structural Motif for Ligand–gated Ion Channels Defined by an Ionotropic ATP Receptor" *Nature* 371:519–523 (Oct. 1994).

FIG. 1
NATIVE LOCUS

FIG. 2
pKNR TARGETING CONSTRUCT

FIG. 3
EXPECTED INTEGRATION

TRANSGENIC ANIMAL MODEL FOR TESTING DRUGS FOR TREATING EATING DISORDERS AND EPILEPSY

STATEMENT AS TO FEDERALLY SPONSORED RESEARCH

This invention was made, at least in part, with a government grant from NIH (Grant No. MH-48200) and from the National Science Foundation (Grant No. BNS-9057377). Thus, the U.S. Government may have certain rights in this invention.

FIELD OF THE INVENTION

This invention relates generally to the field of non-human, transgenic animal models and more particularly to a transgenic mouse model useful in the testing of drugs for their efficacy in the treatment of eating disorders and epilepsy.

BACKGROUND OF THE INVENTION

Serotonin, 5-hydroxytryptamine (5HT), is a biogenic amine that functions as a neurotransmitter Takaki, M., et al., J. Neurosciences 5:1769 (1985), a hormone, Kravitz E. A., et al., J. Exp. Biol. 89:159 (1980), and a mitogen, Nemeck, G. M., et al., Proc. Natl. Acad. Sci. USA 83:674 (1986). Serotonin modulates many forms of synaptic transmission and is believed to exert a number of effects on the growth of neurons in early development. In the spinal cord, serotonin is involved in the inhibitory control of sensory input and in the facilitation of motor output, Fields, H. L., in Advances in Pain Research and Therapy, L. Kruger and J. C. Liebeskind, Eds. (Raven Press, New York, 1984), Vol. 6, pages 241–252, White, S. R. and Neuman, R. S., Brain Res. 188:119 (1980).

In the cortex, transmission at serotonergic synapses contributes to affective and perceptual states, and these synapses represent a major site of action of psychotropic drugs such as LSD, Jacobs, B. L., in Hallucinogens: Neurochemical, Behavioral, and Clinical Perspectives, B. L. Jacobs, Ed. (Raven Press, New York, 1984), pages. 183–202. Serotonergic neurons project to diffuse regions of the brain and exert their physiological effects by binding to cell surface receptors. At least 14 serotonin receptor subtypes (5HT1a–d, 2 and 3) (previously designated 5HT-1A–1D, 2 and 3) have been defined on the basis of their pharmacological properties, Peroutka, S. J., Ann. Rev. Neurosci. 11:45 (1988).

Individual receptor subtypes reveal characteristic differences in their abilities to bind a number of ligands, but the structural basis for the distinct ligand-binding properties is not known. Physiologists and pharmacologists have attempted to specify particular biological functions for some receptor subtypes, but this has met with limited success.

Similarly, the biochemical mechanisms by which these receptors transduce signals across the cell surface have been difficult to ascertain without having well-defined cell populations which express exclusively one receptor subtype. Serotonin receptor subtypes couple to different intracellular second messenger signaling systems, including the regulation of adenylate cyclase activity (5HT1a and 5HT1b) DeVivo, M. and Maayani, S., J. Pharmacol. Exp. Ther. 238:248 (1986); Hoyer, D. and Schoekkter, P., Eur. J. Pharmacol. 147:145 (1988); Weiss, S. et al., Eur. J. Pharmacol. 120:227 (1986), and phospholipase C activities (5HT1c and 5HT2) de Courcelles, D., et al., J. Biol. Chem. 260:7603 (1985); Conn, P. J., et al., Proc. Natl. Acad. Sci. USA 83:4086 (1986). The activation of these second messenger pathways by serotonin modulates the excitable properties of both central and peripheral neurons, Aghajanian, G. K., in Serotonin Neurotransmission and Behavior, B. L. Jacobs and A Gelperin, Eds. (MIT Press, Cambridge, Mass., 1981), pages 156–185; Andrade, R., et al., Science 234:1261 (1986); Andrade, R. and Nicoll, R. A., J. Physiol. 394:99 (1987); Siegelbaum, S. A., et al., Nature 299:413 (1982).

Serotonin receptors are also thought to be linked to the direct modification of ion channel states, and are implicated in mechanisms associated with pain, migraine headaches, and motor control. Moreover, drugs which bind to serotonin receptors may be useful in treating depression. One difficulty which this involves is the prior difficulty in examining a specific interaction of a drug and a specific serotonin receptor alone.

U.S. Pat. No. 4,985,352, issued Jan. 15, 1991 (incorporated herein by reference) discloses a qualitative assay for the introduction of a drug with the serotonin 5HT1c receptor alone. The expression of functional receptors in Xenopus oocytes has provided a sensitive assay for detection of mRNA encoding serotonin receptor, in particular the 5H1c receptor, that couples via inositol phospholipid signaling systems Gunderson, C., et al., Proc. Royal Soc. London, Series B 219:103–109 (1983); Lubbert, H., et al., J. Neurosciences 7:1159–1165 (1987); Takahashi, T., et al., Proc. Natl. Acad. Sci. USA 84:5063 (1987).

Serotonin (5-hydroxytryptamine; 5HT) is a monoaminergic neutransmitter that is believed to modulate numerous sensory, motor, and behavioral processes in the mammalian nervous system, Jacobs, B. L. in *Hallucinogens: Neurochemical, Behavior, and Clinical Perspectives* (eds. Jacobs, B. L.) 183–202 (Raven, N.Y., 1984), Sleight, A. J. Pierce, Pierce, P. A., Schmidt, A. W., Hekmatpanah, C. R. & Peroutka, S. J. in *Serotonin Receptor Subtypes: Basic and clinical aspects*. (eds. Peroutka, S. J.) 211–227 (Wiley-Liss, New York, N.Y., 1991. Wilkinson, L. O. and Dourish, C. T. in Serotonin receptor subtypes: Basic and clinical aspects (eds. Peroutka, S. J.) 147–210 (Wily-Liss, New York, N.Y., 1991).

These diverse responses are elicited through the activation of a large family of receptor subtypes, Tecott, L. H. & Julius, D. J., Curr. Opin. Neurobiol 3,310–315 (1993). The complexity of this signaling system and the paucity of selective drugs have made it difficult to define specific roles for 5HT receptor subtypes, or to determine how serotonergic drugs modulate mood and behavior. To address these issues, we have generated mutant mice.

SUMMARY OF THE INVENTION

A transgenic, non-human animal model is disclosed which lacks receptors which mediate some of the central nervous system (CNS) actions of serotonin. The animal is preferably from a genus selected from the group consisting of Mus (e.g., mice), Rattus (e.g., rats), Oryctologus (e.g., rabbits) and Mesocricetus (e.g., hamsters). More preferably the animal is a mouse which lacks $5HT_{2c}$ receptors. Animals lacking such receptors are overweight due to abnormal control of feeding behavior and are prone to spontaneous death from seizures. Thus, such animals provide an animal model for the testing of drugs which are potentially useful in the treatment of eating disorders and diseases such as epilepsy which result in seizures.

An object of the invention is to provide a non-human animal model which lacks receptors which mediate the central nervous system (CNS) actions of serotonin.

Another more specific object is to provide a small, (less than one kilogram) easily reproducible animal model such as a mouse which lacks $5HT_{2C}$ receptors in sufficient numbers as to result in eating disorders and seizures.

Another object is to provide a useful animal model for the testing of appetite suppressants.

Yet another object is to provide an animal model for testing drugs for their ability to suppress seizures.

A feature of the invention is that the animal models can be designed to lack any or all receptors which mediate the CNS actions of serotonin and the resulting animals screened for effects on eating behavior and/or seizures.

An advantage of the invention is that the animal model displays readily observable abnormalities e.g., obesity and seizures.

These and other objects, advantages and features of the present invention will become apparent to those persons skilled in the art upon reading the details of the DNA constructs, vectors, transgenic non-human animal and assays for using such as more fully set forth below with reference being made to the accompanying figures forming a part thereof.

DETAILED DESCRIPTION OF THE INVENTION

Before the present DNA constructs, vectors, transgenic animals and assays carried out using same are described, it is to be understood that the invention is not limited to the particular constructs, vectors, animals or assays described as such may, of course, vary. It is also to be understood that the terminology Used herein is for the purpose of describing particular embodiments only, and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to the insertion of "a DNA construct" includes the insertion of a large number of such constructs, reference to "an antibody" includes reference to mixtures of antibodies and reference to "the method" includes one or more methods of the type generally described herein and so forth.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

Definitions

The term "transgene" is used herein to describe genetic material which has been or is about to be artificially inserted into the genome of a living animal, preferably a small (less than 1 kg full grown) living mammal. The transgene is inserted in such a manner such that it renders one or more serotonin receptors of the animal inoperative i.e., prevents native genes which make such receptors from being operatively expressed in the animal in such a manner that the resulting animal has eating disorders and/or seizures. A preferred transgene includes genetic material which results in a mutation of a gene for $5HT_{2C}$ receptors and causes both eating disorders and seizures.

The terms "host animal" and more particularly "host mammal" are used to describe animals which are used in the process of the present invention by having their genome genetically and artificially manipulated so as to include a transgene of the invention. For example, preferred host animals include those belonging to a genus selected from Mus (e.g., mice), Rattus (e.g., rats), Oryctolagus (e.g., rabbits), and Mesocricetus (e.g., hamsters) which have their genome artificially and genetically altered by the insertion of genetic material which mutates a gene or genes involved in the expression of one or more serotonin receptors in such a manner as to cause eating disorders and/or seizures. The host animal becomes a transgenic animal of the invention when an exogenous gene is inserted into its genome in sufficient numbers and manner that sufficient numbers of serotonin receptors are not created or are inoperative so that the animal will exhibit eating disorders and/or have seizures.

"Corresponding" means homologous to or substantially equivalent to the designated sequence.

"Genetic material" is a material containing any DNA sequence or sequences either purified or in a native state such as a fragment of a chromosome or a whole chromosome, either naturally occurring or synthetically or partially synthetically prepared DNA sequences, DNA sequences which constitute a gene or genes and gene chimeras, e.g., created by ligation of different DNA sequences.

"Exogenous genetic material" is a genetic material not obtained from or does not naturally form a part of the specific germ cells or gametes which form the particular blastocyst which is being genetically transformed.

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Gene" is the smallest, independently functional unit of genetic material which codes for a protein product or controls or affects transcription and comprises at least one DNA sequence.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype. In connection with the present invention phenotypic expression is the alteration of expression of genetic material wherein a wild-type organism produces a serotonin receptor which alteration results in observable eating disorders (obesity) and/or seizures.

"Zygote" is a diploid cell having the potential for development into a complete organism. The zygote can result from parthenogenesis, nuclear transplantation, the merger of two gametes by artificial or natural fertilization or any other method which creates a diploid cell having the potential for development into a complete organism.

A "blastocyst" is a multicular early embryonic stage of development wherein the embryo begins implantation into the uterine wall.

"Parthenogenesis" is any technique that allows for the development of a female or male gamete into a cell and its development into an organism, which technique is different from the natural development of female and male gametes.

A "replicon" is any genetic element (e.g., a plasmid, a chromosome, a virus) that behaves as an autonomous unit of polynucleotide replication within a cell; i.e., capable of replication under its own control.

A "vector" is a replicon in which another polynucleotide segment is attached, so as to bring about a particular desired result with the attached segment.

A "coding sequence" is a polynucleotide sequence which is transcribed and/or translated into a polypeptide.

A "promoter sequence" is a DNA regulatory region capable of binding RNA polymerase and initiating transcription of a downstream (i.e., in the 3' direction) coding sequence.

A coding sequence is "under the control" of the promoter sequence in a cell when transcription of the coding sequence results from the binding of RNA polymerase to the promoter sequence; translation of the resulting mRNA then results in the polypeptide encoded within the coding sequence.

"Operably linked" refers to a juxtaposition wherein the components are configured so as to perform their usual function. Thus, control sequences operably linked to a coding sequence are capable of effecting the expression of the coding sequence. The present invention involves the insertion of exogenous genetic material which might prevent wild-type genetic material from being operatively linked.

"Control sequences" refers to those sequences which control the transcription and/or translation of the coding sequence(s); these may include, but are not limited to, promoter sequences, transcriptional initiation and termination sequences and translational initiation and termination sequences. In addition, "control sequences" refers to sequences which control the processing of the polypeptide encoded within the coding sequence; these may include, but are not limited to sequences controlling secretion, protease cleavage, and glycosylation of the polypeptide.

"Transformation" is the insertion of an exogenous polynucleotide (i.e., the transgene) into a host cell. The exogenous polynucleotide is integrated within the host genome. In the present invention transformation generally means insertion of exogenous genetic material into the host genome so that wild-type genes encoding a serotonin receptor is altered and the receptor is not created or is inoperative. Specifically, transformation results in phenotypic expression of an eating disorder and/or seizures.

Overview

Transgenic animals of the present invention have actually been produced. More specifically, mice were produced which lacked functional serotonin receptors. Mice were designed that had non-functional $5HT_{2C}$ receptors (prominent G protein-coupled receptors). These are the receptors that are widely expressed throughout the brain and spinal cord. The mice are overweight due to abnormal control of feeding behavior. Further, the mice are prone to spontaneous death from seizures, indicating that receptors such as $5HT_{2C}$ receptors mediate tonic inhibition of neuronal network excitability.

Pursuant to the present invention $5HT_{2C}$ receptor ($5HT_{2C}R$)-deficient mice were generated by introducing a nonsense mutation into exon 5 of the cognate gene, thereby placing a stop codon within the fifth putative transmembrane segment of the receptor and eliminating the carboxy-terminal half of the protein. This is shown by comparing the constructs shown in FIGS. 1 and 2. When this mutation was introduced into the corresponding position of the rat $5HT_{2C}R$ cDNA, the resultant cRNA failed to express functional receptors in Xenopus oocytes. The $5HT_{2C}R$ gene is X-linked Yu, L., et al Mol. Brain Res. 11, 143–149 (1991); Milatovich, A., et al Hum. Molec. Gen. 1, 681–684 (1992), and targeted male (XY) embryonic stem (ES) cells (e.g., J1 and D3) therefore showed disruption of a single allele. This is shown by comparing the constructs of FIGS. 1, 2 and 3.

Brains of Hemizygous mutant male mice (−/Y) were shown to lack $5HT_{2C}Rs$ by two independent tests. Immunocytochemical analysis of coronal sections from brains of wild-type animals using a $5HT_{2C}R$ antiserum revealed staining along the apical surface of the choroid plexus epithelium, where $5HT_{2C}Rs$ are abundantly expressed, Julius, D., MacDermott, A. B., Axel, R. & Jessell, T. M. Science 241, 558–564 (1988); Pompeiano, M., Palacios, J. M. & Mengod, G. Mol. Brain Res. 23, 163–178 (1994). In contrast, sections from mutant animals were devoid of immunoreactivity, even though the choroid plexus exhibited normal morphology and expression of transthyreitin, a cytoplasmic protein that serves as a marker for this tissue, Thomas, T., Power, B., Hudson, P., Schreiber, G. & Dziadek, M. Dev. Biol. 128, 415–427 (1988). In other tests electrophysiological assay in Xenopus oocytes showed that brains of mutant animals lack functional $5HT_{2C}R$ transcripts. Photographs of these sections are shown in a publication which was prepared by the present inventors and entitled "Eating Disorder and Epilepsy in Mice Lacking $5HT_{2C}$ Serotonin Receptors" (Nature, 1995) which is incorporated herein by reference.

Initial inspection of the CNS of $5HT_{2C}R$-deficient animals revealed no gross anatomical or functional abnormalities. No aberrations in ventricular size or brain cytoarchitecture were observed by examination of Nissl-stained sections throughout the neuraxis. Hippocampal long-term potentiation, a form of neural plasticity, was similar when measured in the CA1 and CA3 regions of slice preparations from brains of mutant and wild-type animals. We also examined the sensitivity of these animals to nociceptive stimuli because the distribution of $5HT_{2C}Rs$ has suggested that they participate in pain regulation, Molineaux, S., Jessell, T., Axel, R. & Julius, D. Proc. Natl. Acad. Sci. USA 86, 6793–6797 (1989). Nevertheless, mutant and wild-type animals did not differ in their sensitivities to thermal or mechanical stimulation. Despite the lack of an overt anatomical or physiological phenotype, time revealed that a significant fraction of mutant animals died prematurely as graphically shown in FIG. 5. Deaths were not preceded by any noticeable health problems, such as weight loss, dehydration, or discomfort and autopsies showed no evidence of hemorrhage, infarction, or ischemia that might be associated with cardiovascular failure or stroke.

Continuous videotape monitoring of small groups of animals revealed the occurrence of spontaneous epileptic seizures that were often preceded by repetitive grooming of the snout. This motor activity appeared to generalize so that the animal would fall on its side and progress to seizures characterized by repetitive hyperkinetic (tonic-clonic) movements. In most cases, the animal quickly righted itself after such tonic-clonic seizure and resumed apparently normal behavior. This cycle might then be repeated over the next several minutes. Such episodes occurred sporadically with a frequency not greater than two or three per day. At times, seizures progressed to a tonic extension phase leading to respiratory arrest and death within seconds of seizure onset.

Pharmacological Assay

To provide a more quantitative comparison of relative seizure susceptibilities in mutant and wild-type animals, we employed a pharmacological assay in which mice were infused intravenously with the epileptogenic $GABA_A$ receptor antagonist pentamethylenetetrazole (metrazol). Metrazol infusion elicits a series of stereotyped responses beginning with a period of intermittent twitches of the head and body, leading to tonic-clonic activity, followed by a phase of tonic extension and death, Orloff, M. J., Williams, H. L. & Pfeiffer, C. C. *Proc. Soc. Exp. Biol. Med.* 70, 254–257 (1949). The time (or cumulative drug dose) required for mutant and wild-type animals to progress from one phase of this response to the next was monitored in a blinded fashion and several major differences were seen. These differences are graphically shown in FIGS. 6 and 7. Mutants showed a 24% reduction in seizure threshold (onset of first twitch response), an 83% reduction in the duration of the tonic-clonic phase, and a 48% reduction in the lethal dose, relative to wild-type controls. These results suggest that the loss of $5HT_{2C}R$ function leads to both a lowered seizure threshold and a more rapid progression of seizure activity.

Figure 7:
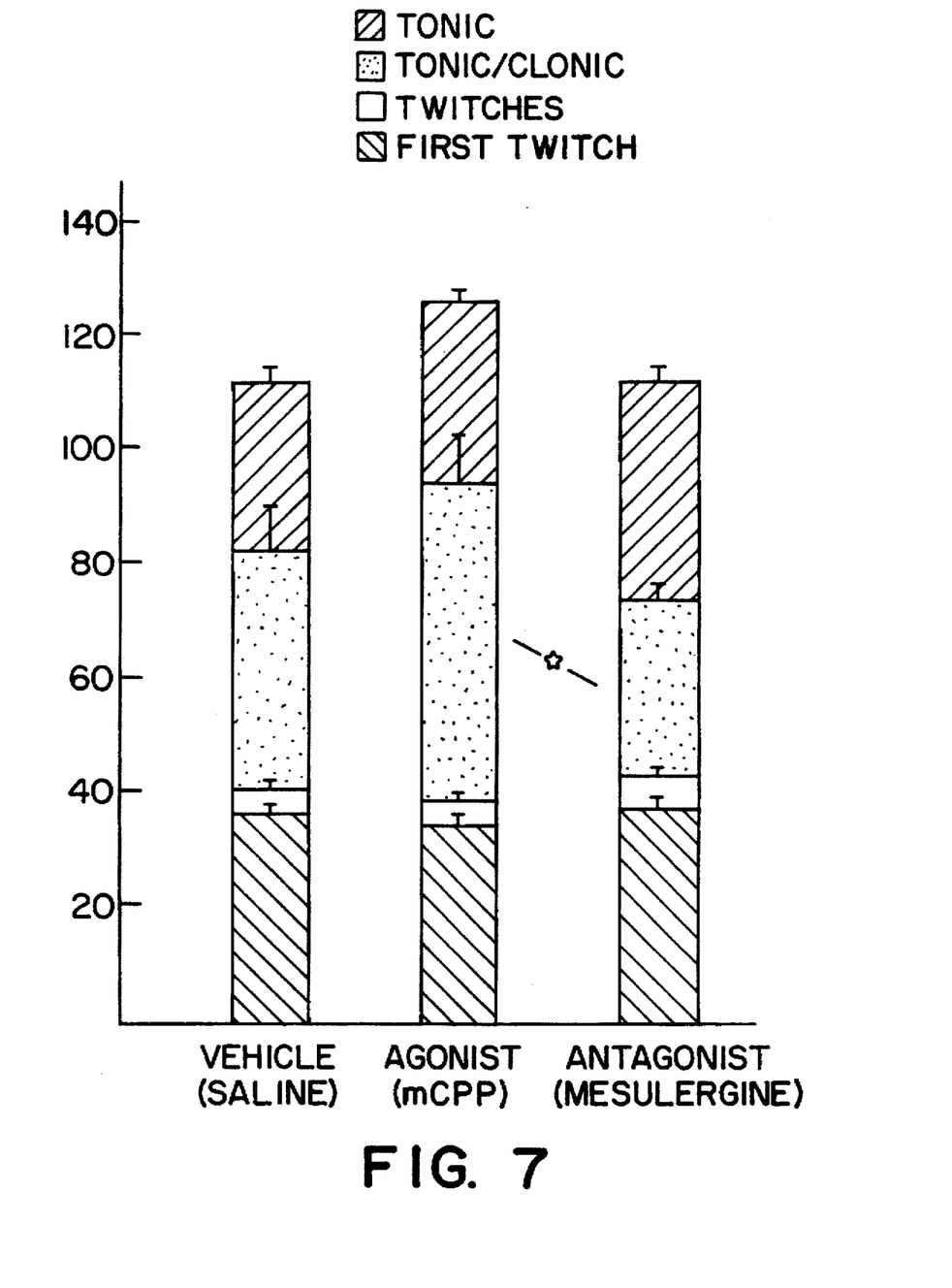
FIG. 7 is a bar graph as per FIG. 6 showing effects of certain classes of drugs.

To determine whether this difference between mutant and wild-type animals can be mimicked in normal animals by pharmacological manipulation, we administered metrazol to C57B1/6J mice that has been pretreated with 1-(3-Chlorophenyl)piperazine (mCPP), a non-selective $5HT_{2C}R$ agonist, or with mesulergine, a non-selective antagonist. The duration of the tonic-clonic phase of the seizure response was significantly greater in animals pretreated with agonist compared to those pretreated with antagonist. This is shown in FIG. 7. This result supports the hypothesis that the epileptic phenotype exhibited by $5HT_{2C}R$-deficient mice does not arise from indirect developmental or compensatory changes in the brain due to loss of $5HT_{2C}R$ activity, but instead reflects a normal adult function of this receptor to suppress neuronal network excitability.

Eating Disorders

Figure 8:
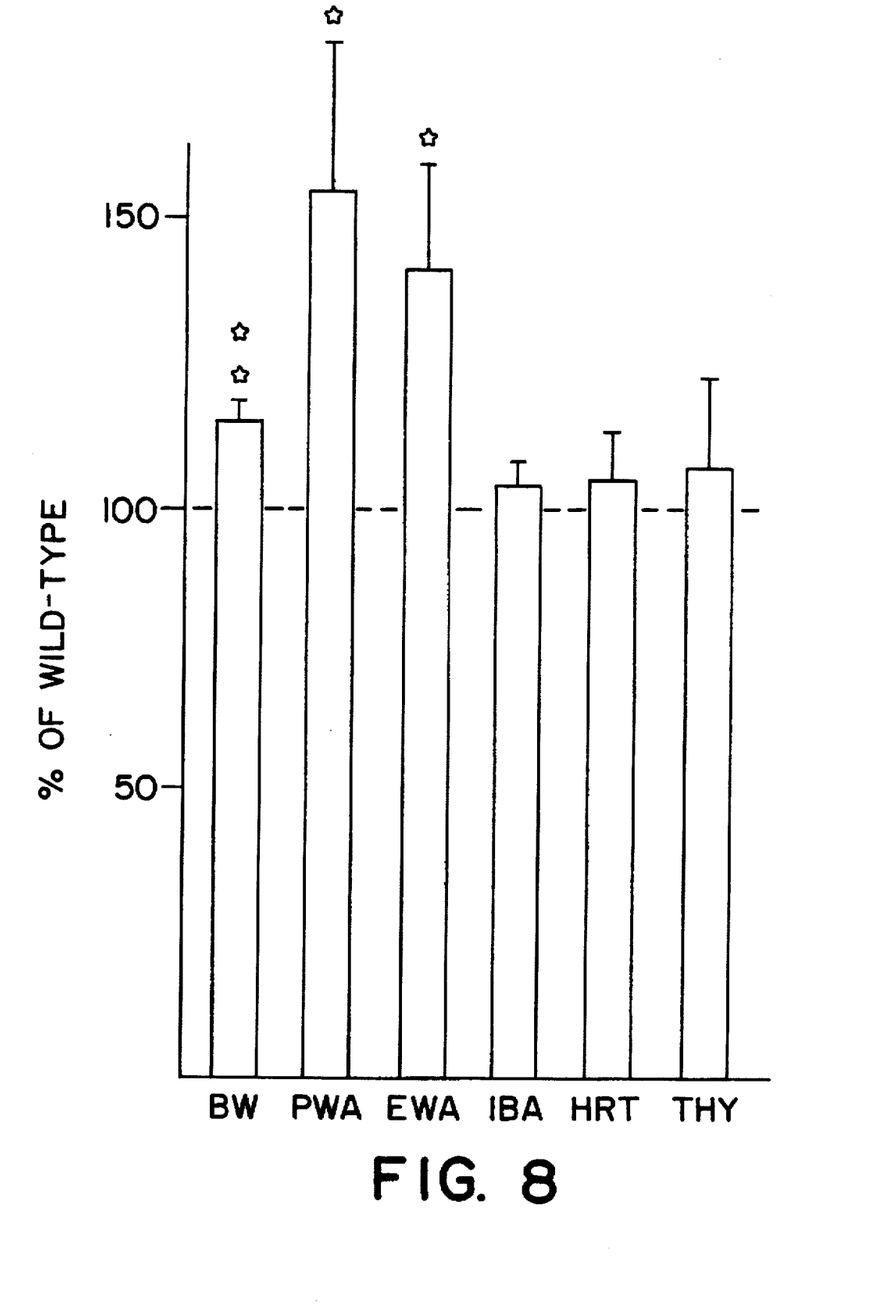
FIG. 8 is a bar graph of wild-type and mutant mice.

Serotonergic drugs have a known effect in the modulation of appetite, Jacobs, B. L. in *Hallucinogens: Neurochemical, Behavioral, and Clinical Perspectives* (eds. Jacobs, B. L.) 183–202 (Raven, N.Y., 1984), Blundell, J. E., *Am. J. Clin. Nutr.* 55, 155S–159S (1992), Wurtman, J., et al., *Neuropsychopharm.* 9, 201–210 (1993). Such is interesting when combined with the observation that mutant mice were often heavier than their normal littermates. In rare instances, mutants grew to be twice as heavy as their wild-type siblings, attaining weights of up to 82 grams. To quantitatively determine whether the loss of $5HT_{2C}Rs$ resulted in elevated body weight, seven litters, each consisting of at least two hemizygous mutant males and two wild-type males, were used for analysis of body and organ weights. This is shown in FIG. 8 showing a significant (13%) increase in average total body weight of mutant animals compared to wild-type siblings, with no difference in body length. Mutant animals also had larger fat stores, as exemplified by a 48% increase in the deposition of perirenal white adipose tissue. Brown adipose tissue, which is primarily involved in thermoregulation, was not significantly altered in mutant animals.

Some non-selective serotinergic agonists with relatively high affinities for $5HT_{2C}Rs$ (mCPP for example) have been shown to act as appetite suppressants, Samanin, R., et al., *Schm. Arch. Pharmacol.* 308, 159–163 (1979); Kennett, G. A. & Curzon, G. *Br. J. Pharmacol.* 103, 2016–2020 (1991); Kitchener, S. J. & Dourish, C. T. *Psychopharm.* 113, 369–377 (1994). To determine whether this effect is specifically mediated through activation of $5HT_{2C}Rs$, a comparison was carried out on the appetite suppressant actions of mCPP on wild-type and mutant animals. The comparison showed that mCPP drastically reduced food intake by wild-type mice (78%). However, there was no effect on the amount of food consumed by mutant animals demonstrating that the $5HT_{2C}R$ is the primary site at which this non-selective serotonergic drug exerts its appetite-suppressant action (see FIG. 9).

Transgenes

In general, the transgene is any exogenous genetic material integrated (or to be integrated) into the genome of an animal in such a manner as to result in a material mutation in a gene or genes which express a serotonin receptor which mutation results in an eating disorder and/or seizures. Thus, a transgene may be any genetic material including a single base which is added to a gene expressing a serotonin receptor. The exogenous material is preferably inserted in a protein coding region or in a stop codon in a non-coding region.

A transgene may result from the deletion of genetic material from a gene coding for a serotonin receptor if the deletion materially effects the gene and results in an eating disorder or seizures.

Transgenic Animal Produced

The transgenic organisms of the invention all include within a plurality of their cells a cloned recombinant or synthetic DNA sequence which prevents expression of a native DNA sequence and thereby results in an eating disorder and/or seizures. More specifically, the transgenic organisms contain specific sequences of exogenous genetic material, such as the sequences described above in detail which are comprised of a stop codon inserted in a gene for $5HT_{2C}$ in such a manner as to prevent normal expression of the gene (see FIGS. 2 and 3). Since it is possible to produce transgenic organisms of the invention utilizing a variety of different sequences, a general description will be given of the production of transgenic organisms by referring generally to exogenous genetic material. This general description can be adapted by those skilled in the art in order to incorporate the DNA sequences (e.g., stop codon) into organisms (e.g. small mammals such as mice) and prevent or disrupt expression of those sequences which naturally result in the expression of a functioning serotonin receptor. For more details regarding the production of transgenic organisms, and specifically transgenic mice, refer to Sandou, et al., *Science* Vol. 265, 1875–1878 ) (Sep. 23, 1994); U.S. Pat. Nos. 4,873,191, issued Oct. 10, 1989 and 5,387,742, issued Feb. 28, 1995 (incorporated herein by reference to disclose methods producing transgenic mice), and to the numerous scientific publications referred to and cited therein.

Making Transgenic Animals

Figure 1:
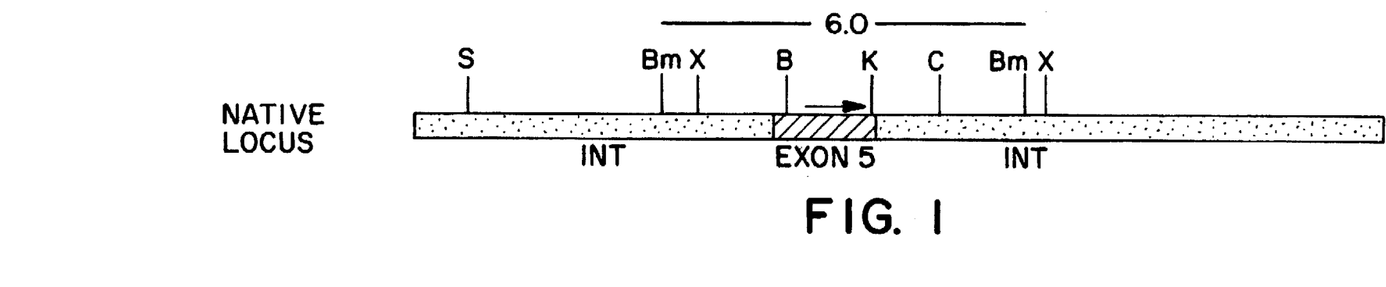
FIG. 1 shows a schematic representation of genetic material for the $5HT_{2C}R$ gene.

Transgenic animals of the present invention are produced by the application of procedures which result in an animal with a genome that incorporates exogenous genetic material which is integrated into the genome in such a manner as to disrupt the normal formation of a serotonin receptor. The procedure involves obtaining genetic material, or a portion thereof, which encodes a serotonin receptor. A specific example of such material in the form of a linear sequence of DNA encoding for a portion of $5HT_{2C}$ is shown in FIG. 1 as the "Native Locus." The isolated native sequence is then genetically manipulated by the insertion of exogenous genetic material such as a stop codon and non-coding sequence shown respectively as "X-ST" and "NEO" in the construct shown in FIG. 2 and labelled "pKNR Targeting Construct."

Figure 2:
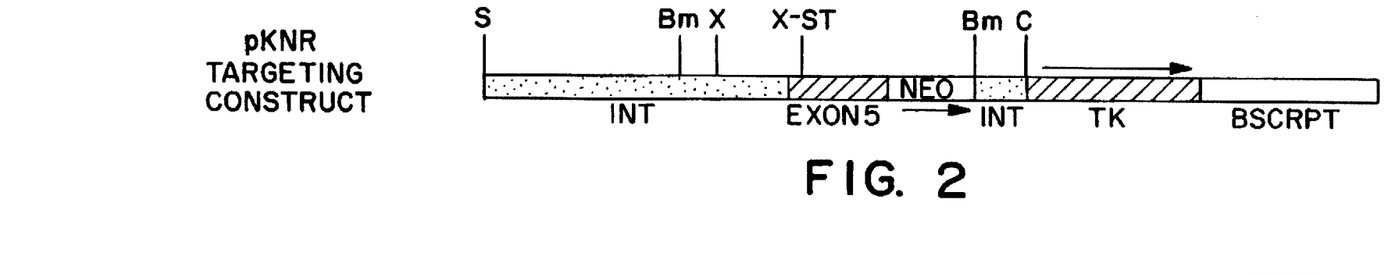
FIG. 2 is a schematic representation of the pKNR targeting construct.

The manipulated construct of FIG. 2 is then inserted into an embryonic or ES stem cell line. The insertion is made using electro-potation. The cells subjected to electro-poration are screened (e.g., Southern bolt analysis) to find positives i.e., cells which have integrated into their genome as per the construct of FIG. 3. The positive cells (e.g., those which are integrated as per FIG. 3) are isolated, cloned and injected into blastocysts obtained from a host animal of the same species. For example, positive cells are injected into 3.5 day old blastocysts from mice. The blastocysts are then inserted into a female host animal and allowed to grow to term. The offsprings of the female are tested to determine which animals were transgenic e.g., included the inserted exogenous DNA sequence and which were wild-type. A more detailed description of producing a specific transgenic mouse is provided in Examples 1 and 2.

Obesity-Underlying Mechanisms

Two types of mechanisms have been proposed to underlie obesity in various rodent models. The first involves metabolic defects in which there is an increased predisposition to store calories in white adipose fat depots. The second involves behavioral abnormalities that lead to increased food consumption in the setting of a normal metabolic state. These two mechanisms can be distinguished by a standard paired feeding analysis, Parkinson, W. L. & Weingarten, H. P. *Am. J. Physiol.* 259, R829–R835 (1990).

At the time of weaning, mutant animals were paired with wild-type littermates. Wild-type animals had ad libitum access to food, whereas each mutant animal was provided only the amount of food consumed by its wild-type partner. After 4 weeks, animals were analyzed for body weight, length, and organ weights. If the overweight phenotype is due to a metabolic defect, then calories will be stored in fat depots at the expense of linear growth. As a result, mutant animals would be shorter than their wild-type littermates and have elevated fat stores. In the case of a behavioral abnormality, restricted feeding would normalize body composition of mutant animals relative to their paired wild type littermates.

The results (as shown in Table 1) show that behavioral abnormalities were the cause of the obesity. This conclusion can be reached because body weight, length, and white adipose tissue depots of pair-fed mutants were not significantly different from wild-type controls, nor were plasma levels of glucose and insulin (see Table 1).

TABLE 1

Restricted feeding analysis reveals a behavioral eating disorder.

|  |  | Fed Ad-Libitum | Pair-Fed & Fasted |
|---|---|---|---|
| Body Weight (gm) | WT | 32.5 ± 1.0 (18) | 23.4 ± 0.9 (9) |
|  | MU | 36.1 ± 1.6 (21) | 22.2 ± 0.8 (9) |
| Body Length (mm) | WT | 95.0 ± 0.8 (8) | 86.9 ± 0.8 (9) |
|  | MU | 95.6 ± 1.6 (9) | 86.0 ± 0.8 (9) |
| Plasma Glucose (mg/dl) | WT | 145 ± 9 (14) | 143 ± 11 (9) |
|  | MU | 144 ± 8 (15) | 160 ± 11 (9) |
| Plasma Insulin (ng/ml) | WT | 3.4 ± 1.5 (14) | 1.2 ± 0.3 (9) |
|  | MU | 6.9 ± 3.5 (15) | 1.5 ± 0.7 (9) |

Body weights and lengths, and glucose and insulin levels were determined for wild-type (WT) and $5HT_{2c}$ receptor-mutant (MU) mice that had been fed ad libitum (ages 11–15 weeks), or pair-fed (MU to WT) for 4 weeks post-weaning and fasted overnight prior to morning sample collection. Mean data are accompanied by ± standard error of the mean (numbers of mice). Values representing significant differences between wild-type and mutant animals (P ≦ 0.01) are shaded. For paired feeding studies, 9 pairs of individually-housed mice, each consisting of 1 mutant and 1 wild-type littermate, were established at the time of weaning (3 weeks). Wild-type animals had ad libitum access to food, whereas each day mutant animals were provided only the amount of food consumed by their wild-type partners. Values were determined as in FIG. 3.

This contrasts with the ad libitum situation, in which mutant animals were heavier than their wild-type siblings, but of the same length (see FIG. 8 and Table 1). The elevated variance in insulin levels of mutant animals fed ad libitum most likely reflects variations in the interval between eating and the collection of serum samples. This is verified by the normalization of insulin levels following an overnight fast (Table 1), and contrasts with the elevated insulin levels commonly seen in rodent metabolic obesity syndromes, Parkinson, W. L. & Weingarten, H. P. *Am. J. Physiol.* 259, R829–R835 (1990). Finally, levels of brown adipose tissue uncoupling protein, an indicator of sympathetic nervous system activity, were normal in mutant animals fed ad libitum. Decreased sympathetic nervous system drive to brown adipose tissue frequently accompanies metabolic obesity, Himms-Hagen, J. *Front Neuroendocrinol.* 12, 38–93 (1991).

$5HT_{2C}$ Receptors-Function

The distribution of $5HT_{2C}Rs$ and the actions of non-selective drugs have prompted speculation that this serotonin receptor subtype participates in processing and integration of sensory information, regulation of central monoaminergic systems, and modulation of neuroendocrine responses, anxiety, feeding behavior, and cerebrospinal fluid production.

The unexpected observation of an epileptic phenotype in mice devoid of $5HT_{2C}Rs$ now implicates this subtype in the modulation of neuronal network excitability, consistent with prior observations that changes in serotonergic systems can alter the threshold for seizure activity, Kilian, M. & Frey, H. H. *Neuropharm.* 12, 681–692 (1973); Jobe, P. C., Picchioni, A. L. & Chin, L. *Life Sci.* 13, 1–13 (1973); Sparks, D. L. & Buckholtz, N. S. *Pharmacol. Biochem. Behav.* 23, 753–757 (1985); Dailey, J. W., Slater, L., Crable, D. J. * Jobe, P. C. *Fed. Proc.* 46, 2282 (1987). Within CNS neurons, highest levels of $5HT_{2C}R$ transcripts are found in the hippocampus, a temporal lobe structure that is a common focus for seizures involving stereotyped or repetitive movements, Engel, J., *Seizures and epilepsy* (S. A. Davis, Philadelphia, 1989) such as the repetitive snout cleaning observed with mice of the present invention. Regardless of the location of the seizure focus, this genetic model has several features in common with some forms of human epilepsies (the onset of seizure episodes is spontaneous and not readily inducible and the occurrence infrequent and sporadic), providing a new potential mechanism for seizure genesis and rationale for the development of anticonvulsant agents.

The transgenic mice of the present invention demonstrate that the $5HT_{2C}R$ plays an important role in the serotonergic control of feeding and appetite, and that diminished serotonergic signaling in $5HT_{2C}R$ mutant mice leads to increased food intake due to a behavioral disorder, rather than a metabolic abnormality. Drugs such as fluoxetine (Prozac) and dexfenfluramine, which enhance serotonergic transmission by blocking transmitter reuptake, have recently been shown to control overeating associated with certain obesity syndromes, Wurtman, J. et al., *Neuropsychopharm.* 9, 201–210 (1993). Moreover, $5HT_{2C}R$ transcripts have been detected in the paraventricular nucleus of the hypothalamus, lesions of which result in a behavioral obesity syndrome. Thus, in contrast to other rodent models of obesity, such as oh/oh and db/db mice (reviewed in refs., Friedman, J. M. & Leibel, R. L. *Cell* 69, 217–220 (1992); Flier, J. S. *Cell* 80, 15–18 (1995).), $5HT_{2C}R$-deficient mice represent a model for the analysis of weight regulation mechanisms that are primarily behavioral in nature and therefore provide a novel tool for elucidating defects in neurochemical pathways that underlie the abnormal control of appetite observed in mood and eating disorders.

EXAMPLES

The following examples are put forth so as to provide those of ordinary skill in the art with a complete disclosure and description of how to make the constructs, vectors, transgenic animals and assays of the present invention and are not intended to limit the scope of what the inventors regard as their invention. Efforts have been made to ensure accuracy with respect to nomenclature and numbers used (e.g., amounts, temperature, etc.) but some experimental errors and deviation should be accounted for. Unless indicated otherwise, parts are parts by weight, molecular weight is weight average molecular weight, temperature is in degree centigrade, and pressure is at or near atmospheric.

EXAMPLE 1

Targeted Mutation of the $5HT_{2C}$ Receptor Gene

Figure 3:
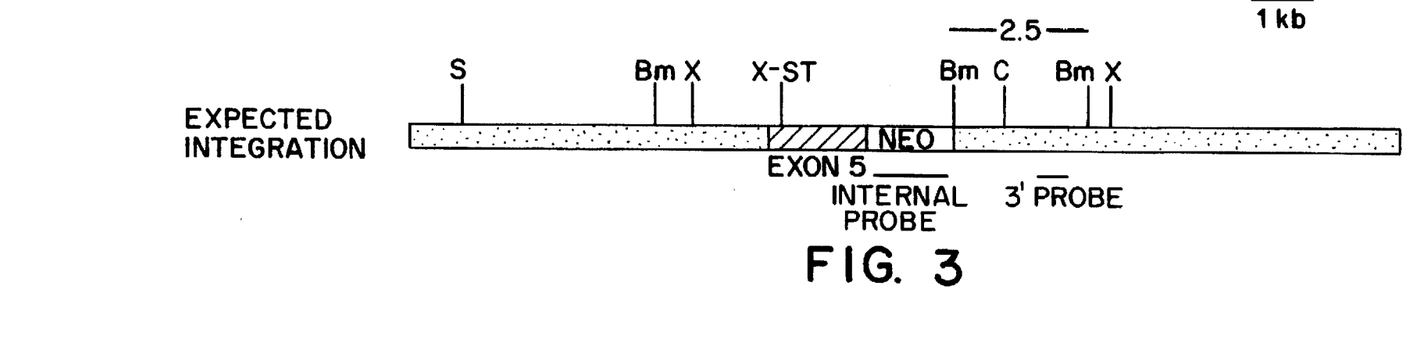
FIG. 3 is a schematic representation of the expected targeted allele.
Figure 4:
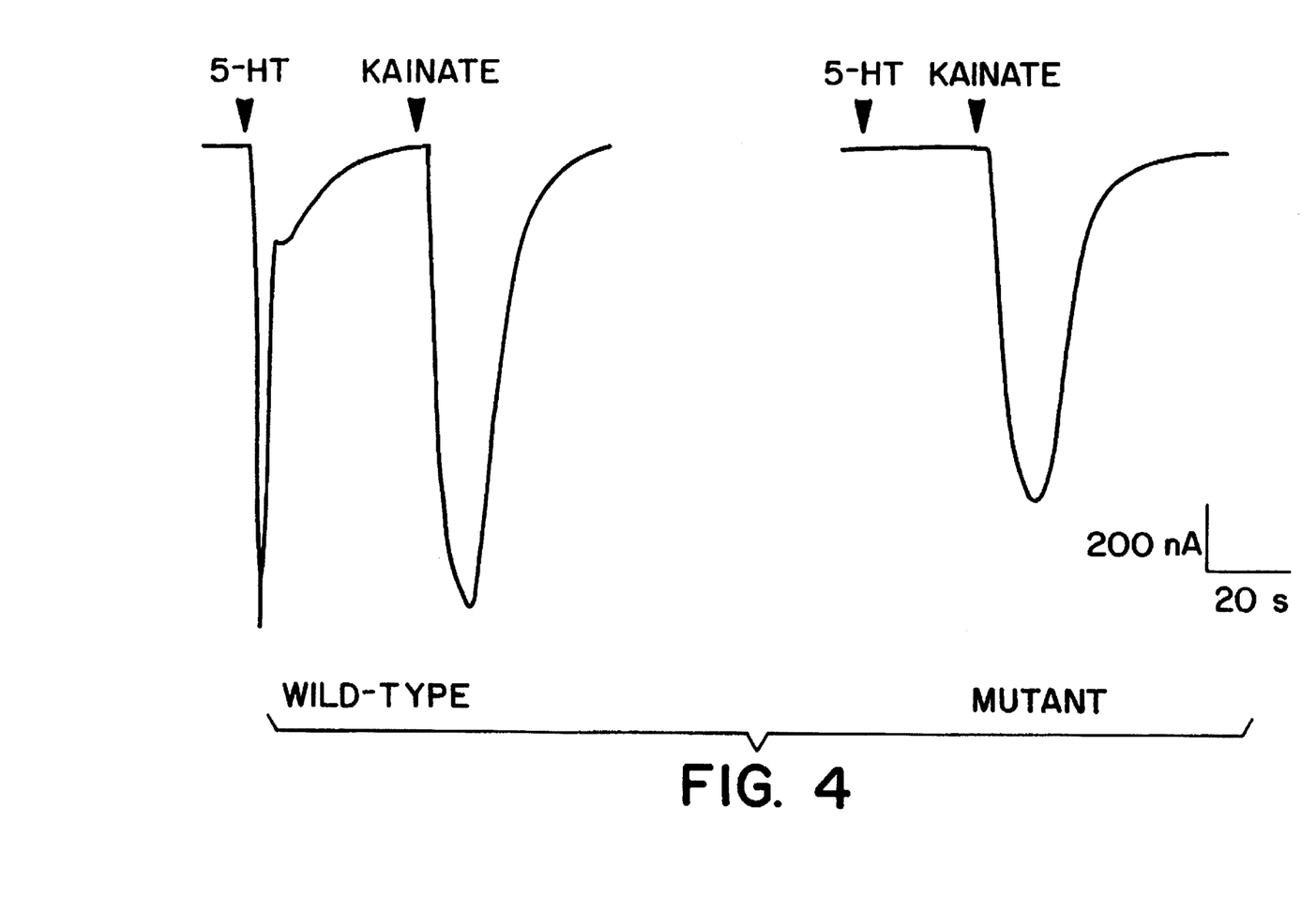
FIG. 4 shows graphs of (a wild-type mouse and a mutant) whole-cell voltage-clamp recordings in xenopus oocytes.

FIG. 1 provides a schematic representation of a portion of the $5HT_{2C}R$ gene, FIG. 2 shows the pKNR targeting construct, and FIG. 3 shows the expected targeted allele. To create a nonsense mutation, a 16 bp oligonucleotide (CTAGTCTAGACTAGCC) containing stop codons in three reading frames and an XbaI recognition site (X-ST) was inserted into the Bsm I site (B) of exon 5. Aa neomycin resistance cassette (NEO) was inserted into the Kpn I (K) site of the exon. The mutated fragment was cloned into the pGK-TK plasmid, which contains the HSV thymidine kinase gene driven by the PGK promoter (TK) in a Bluescript (BSCRPT) vector (Stratagene). Locations of 3' flanking and internal probes for Southern blot analysis are indicated. Southern blot analysis of Bam HI (Bm)-digested genomic DNA from double drug selected ES cell transfectants, and from tails of littermates produced from crossing a female heterozygous mouse with a wild-type male as carried out to find positive cells. Blots were hybridized with a 3' flanking probe. Wild-type and mutant alleles correspond to 6.0-kb and 2.5-kb fragments, respectively. Immunocytochemical analysis was carried out using an antibody to the C-terminal tail of the $5HT_{2C}R$ revealed staining along the apical membrane of the choroid plexus epithelium of wild-type, but not mutant mice. Choroid plexuse of mutant and wild-type animals were indistinguishable when stained with antibody to transthyreitin (anti-TTR) or with hematoxylin and eosin (H & E). Whole-cell voltage-clamp recordings revealed a marked inward current following bath application of serotonin to Xenopus oocytes injected with poly(A) $^+$RNA from brains of wild-type mice. No detectable current was observed with mRNA from mutant siblings. As a positive control, application of kainate, a glutamate receptor agonist, evoked inward currents of similar magnitude in both cases.

EXAMPLE 2

Producing A Transgenic Mouse

An 8.5 kb DNA fragment containing exon 5 of the $5HT_{2C}R$ gene was isolated from a 129/Sv mouse genomic library and use to construct the pKNR targeting vector. ES cells were electroporated with linearized pKNR and a positive-negative selection procedure, Mansour, S. L., Thomas, K. R. & Capecchi, M. R. *Nature* 336, 348–352 (1988) was used to enrich for targeted clones. Surviving ES cell colonies were screened for homologous recombination events by Southern bolt analysis and targeted clones were obtained with an overall frequency of 1/45. Male chimeras produced by injection of these cells into C57Bl/6J blastocysts were bred with B6D2 mice and germ line transmission of the mutation was achieved with independent clones. Female heterozygotes were mated to wild-type siblings or C57Bl/J6 males to produce hemizygous mutant males bearing a single disrupted allele of the $5HT_{2C}R$ gene. Expected distributions of gender and targeted mutation were observed among progeny. For immunocytochemistry, an affinity-purified polyclonal antiserum was raised against a synthetic peptide (CVVSERISSV) corresponding to the C-terminal tail of the $5HT_{2C}R$. Brains of mutant and wild-type littermates were fixed and sectioned (13 µM thickness). See Tecott, L., Maricq, A. & Julius, D. *Proc. Natl. Acad. Sci. USA* 90, 1430–1434 (1993). Immunostaining was performed using an avidin-biotinylated peroxidase complex (ABC kit, Vector Laboratories). Messenger RNA preparation and oocyte electrophysiology were carried out. See Brake, A. J., Wagenbach, M. J. & Julius, D. *Nature* 371, 519–523 (1994). Oocytes were injected with 50 ng poly(A) $^+$RNA from the brains of wild-type or mutant siblings. Responses were evoked with 10 second pulses (arrow heads) of serotonin (10 µM) or Kainate (100 µM), at a holding potential of −80 mV.

EXAMPLE 3

Pharmacological Assay-Seizures

Figure 5:
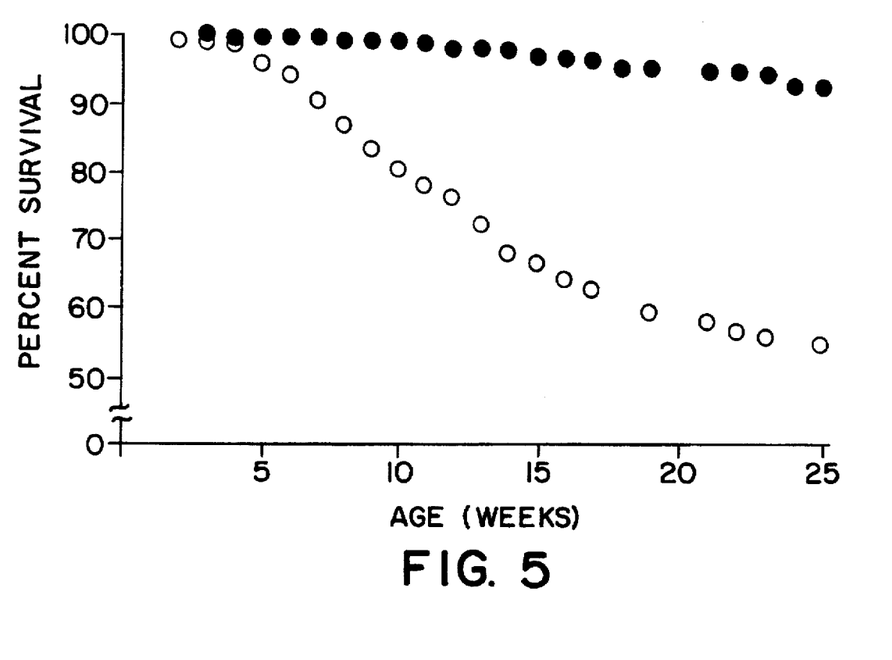
FIG. 5 shows a graph of the survival of wild-type and mutant mice over a period of 25 weeks.
Figure 6:
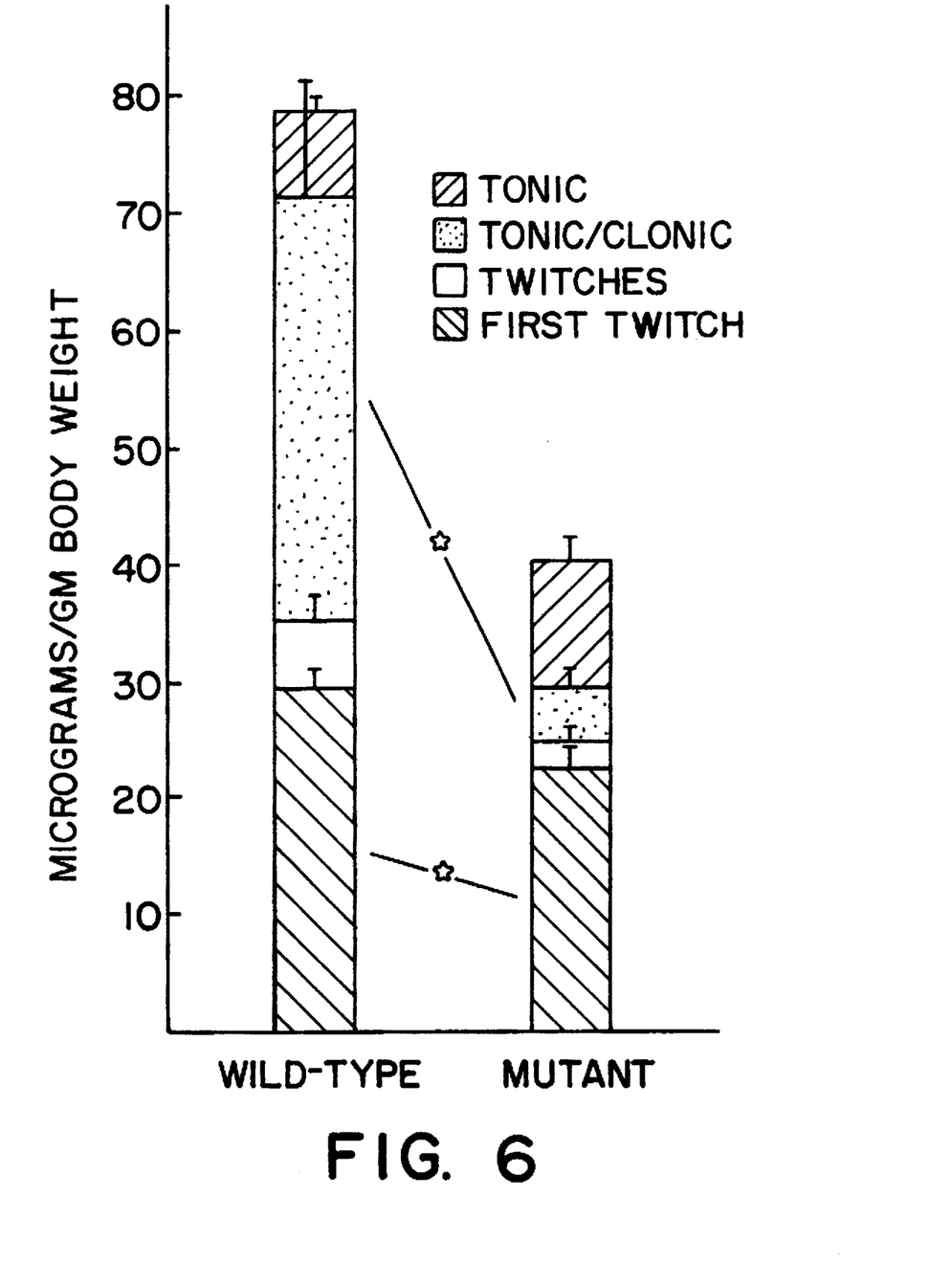
FIG. 6 is a bar graph of wild-type and mutant mice showing stages of the seizure response as related to amount of drug given.

Mice were loosely held in a plexiglass restrainer and administered a continuous infusion of 0.5% metrazol in PBS into the tail vein at a constant rate of 0.36 ml/min. Experimenters were blinded to the genotype of the animal and drug administered. As shown in FIG. 5 spontaneous deaths among hemizygous mutant male mice were first seen in the fifth postnatal week. Filled and open dots represent wild-type and mutant animals, respectively. As shown in FIG. 6 threshold and latency following the timed intravenous infusion of pentamethylenetetrazole (metrazol) are reduced in mutant male mice compared to wild-type littermates. Wild-type (n=10) and mutant (n=13) male mice (11-15 weeks old) received a continuous infusion of metrazol into the tail vein at a constant rate. The time required for the animals to progress from one phase to the next was monitored. Data were corrected for body weight and converted to the corresponding metrazol dose. Stages include latency to first twitch (black), isolated twitches of the head and body (open), hyperkinetic tonic-clonic seizures (stippled), and tonic extension (gray). Values represent mean+SEM. *p≦0.005. As shown in FIG. 7 the tonic-clonic phase of a metrazol-induced seizure in normal mice is extended by pretreatment with a serotonergic antagonist relative to pretreatment with agonist. C57B1/6J mice were administered metrazol 30 minutes after intraperitoneal injection with agonist (mCPP; 5 mg/kg) (n=10), antagonist (mesulergine; 2 mg/kg) (n=11), or saline (vehicle) (n=14). Values represent mean+SEM. *P≦0.02.

EXAMPLE 4

Appetite Suspension

Adult mice (11-15 weeks old) from 7 litters were sacrificed early in the light cycle, and tissue and blood samples were collected for the determination of weights, uncoupling protein content of brown adipose tissue, glucose and insulin values. All measurements were made as previously described, Strack, A. M., Bradbury, M. J. & Dallman, M. F. AM. J. Physiol. in the press, except that insulin levels were determined using a Linco radioimmunoassay kit (St. Charles, Mo.). For mCPP trials, mutant (n=13) and wild-type (n=12) male mice were administered (in blinded fashion) either mCPP (5 mg/kg i.p.) or vehicle (saline) following an 18 hour overnight fast. Thirty minutes after injection, food was provided and consumption over the ensuing 2 hour period was measured. One week later, the procedure was repeated, except that mice that received mCPP on the previous week received vehicle, and vice versa. Each animal therefore served as its own baseline control. Food consumed following mCPP administration is expressed as percentage of consumption following vehicle administration.

As shown in FIG. 8 mutant mice showed significantly greater body weight (BW), perirenal white adipose tissue (PWA) and epididymal white adipose tissue (EWA) deposits compared to wild-type siblings. Interscapilar brown adipose tissue (IBA), heart (HRT), and thymus (THY) weights did not differ significantly between wild-type and mutant animals. Mean values for mutant animals of each litter are expressed as a percentage of the values for wild-type littermates. Values represent mean+SEM. *P≦0.05; **P≦0.01.

Figure 9:
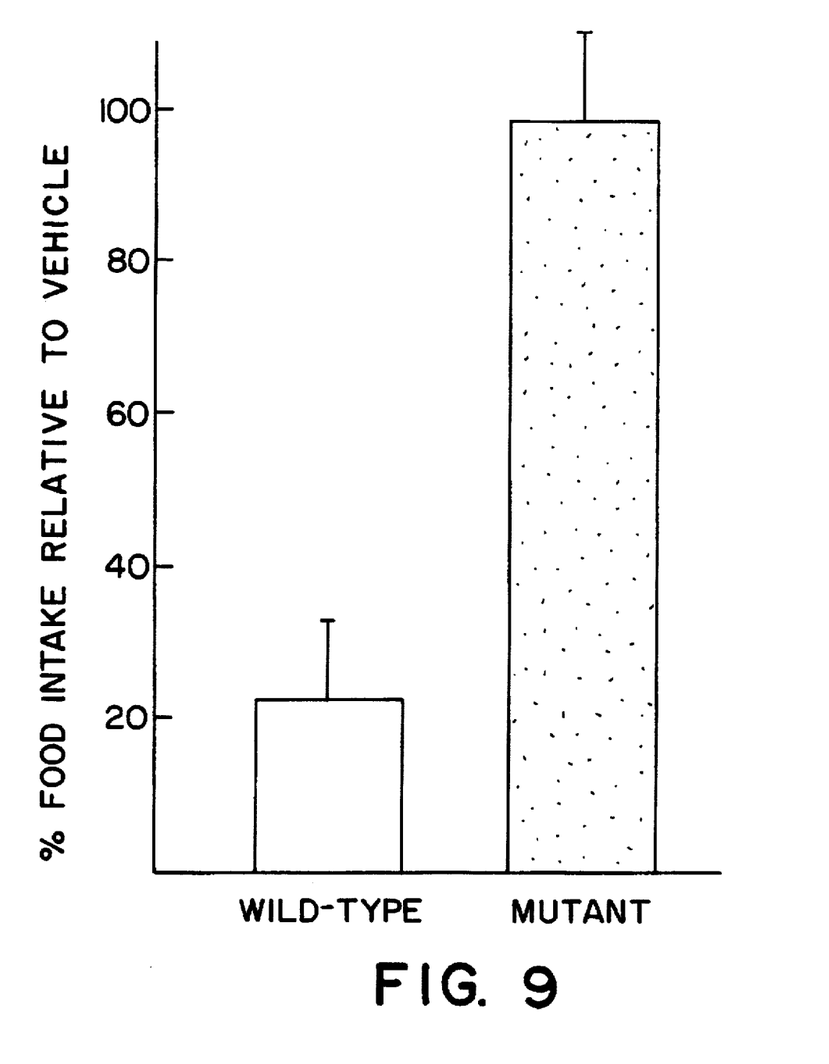
FIG. 9 is a bar graph re mutant and wild-type mice.

FIG. 9 shows that $5HT_{2C}$R-deficient mice do not respond to the appetite suppressant actions of the serotonergic agonist mCPP. Food consumption was measured in wild-type and mutant animals after administration of mCPP. For each animal, values were normalized to separate "sham" trials in which only saline was administered prior to feeding. mCPP drastically reduced food intake by wild-type animals, but not $5HT_{2C}$-R mutants. Values represent mean+SEM. P≦0.001.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

What is claimed is:

1. A male transgenic mouse comprising a disrupted allele of the $5HT_{2C}$ serotonin receptor gene, wherein said disruption has been introduced into its genome via homologous recombination with a DNA targeting construct in an embryonic stem cell, and wherein said disruption results in the lack of expression of a functional $5HT_{2C}$ serotonin receptor, and further wherein said transgenic mouse exhibits seizures; has an eating disorder which results in increased food consumption relative to a mouse lacking said disrupted allele; and wherein the appetite of said transgenic mouse is not suppressed by mCPP.

2. The transgenic mouse of claim 1, wherein said disrupted allele comprises a stop codon that disrupts expression of a functional $5HT_{2C}$ serotonin receptor.

3. The transgenic mouse of claim 1, wherein said disrupted allele comprises a deletion disrupting said $5HT_{2C}$ receptor gene.

4. A method of producing the transgenic mouse of claim 1 comprising:

(a) transfecting a population of mouse embryonic stem cells with a DNA molecule comprising a disruption of the $5HT_{2C}$ serotonin receptor gene;

(b) identifying a mouse embryonic stem cell having said disruption of the $5HT_{2C}$ serotonin receptor gene integrated into its genome by homologous recombination;

(c) inserting said cell into a mouse embryo; and (d) allowing the resulting embryo to grow thereby producing the transgenic mouse of claim 1.

5. The method of claim 4, wherein said DNA molecule comprises a stop codon inserted in exon 5 of said $5HT_{2C}$ receptor gene, thereby preventing expression of the carboxy-terminal portion of the $5HT_{2C}$ receptor.

6. The method of claim 4, wherein said DNA molecule comprises a deletion disrupting said $5HT_{2C}$ receptor gene.

* * * * *